(12) United States Patent
Auer

(10) Patent No.: US 7,590,551 B2
(45) Date of Patent: Sep. 15, 2009

(54) SYSTEM AND METHOD FOR PROCESSING PATIENT INFORMATION

(75) Inventor: John E. Auer, Ipswich, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 1575 days.

(21) Appl. No.: 09/942,516

(22) Filed: Aug. 30, 2001

(65) Prior Publication Data
US 2002/0091309 A1    Jul. 11, 2002

Related U.S. Application Data

(60) Provisional application No. 60/249,576, filed on Nov. 17, 2000.

(51) Int. Cl.
*G06F 19/00*    (2006.01)
(52) U.S. Cl. .................... 705/3; 705/2; 600/300; 600/301; 600/483; 707/8; 707/104.1; 345/545; 345/3.1; 709/202; 128/204.21; 128/204.18
(58) Field of Classification Search .......... 705/2, 705/3; 600/300, 301, 483; 707/8, 104.1; 345/545, 3.1; 709/202; 128/204.21, 204.18
See application file for complete search history.

(56) References Cited

U.S. PATENT DOCUMENTS

| | | | |
|---|---|---|---|
| 4,191,962 A | 3/1980 | Sramek | 346/110 |
| 4,634,426 A | 1/1987 | Kamen | 604/65 |
| 4,956,640 A * | 9/1990 | Jundanian et al. | 345/545 |
| 5,004,472 A | 4/1991 | Wallace | 606/194 |
| 5,056,059 A | 10/1991 | Tivig et al. | 364/900 |
| 5,077,666 A * | 12/1991 | Brimm et al. | 705/2 |
| 5,107,831 A | 4/1992 | Halpern et al. | 128/204.26 |
| 5,262,944 A * | 11/1993 | Weisner et al. | 600/300 |
| 5,325,478 A | 6/1994 | Shelton et al. | 395/148 |
| 5,337,405 A | 8/1994 | Lindauer et al. | 395/147 |
| 5,361,202 A | 11/1994 | Doue | 364/413.01 |

(Continued)

FOREIGN PATENT DOCUMENTS

WO    WO98/50095 A    11/1998

OTHER PUBLICATIONS

Michael P. Dosch, "The Anesthesia Gas Machine, Vaporizers, Compressed Gases, Safety: Avoiding the Pitfalls," *University of Detroit Mercy Graduate Program in Nurse Anesthesiology*, Pontiac, Michigan, pp. 33; http://www.gasnet.org/education/machine; May 28, 2000.

(Continued)

*Primary Examiner*—C. Luke Gilligan
*Assistant Examiner*—Dilek B Cobanoglu
(74) *Attorney, Agent, or Firm*—Jack Schwartz & Associates, PLLC

(57) ABSTRACT

A system and method for displaying medical information derived from a plurality of sources is described. Medical data associated with a patient are acquired from at least one of the plurality of sources on the network. The acquired data are prioritized for display in a desired order and/or time frame. A menu generator is used for generating a composite window for displaying the ordered acquired data in a first window together with at least one of user-entered medical notes, medical laboratory results and ventilator data in a second window.

21 Claims, 5 Drawing Sheets

U.S. PATENT DOCUMENTS

| | | | |
|---|---|---|---|
| 5,404,292 A * | 4/1995 | Hendrickson | 600/301 |
| 5,441,047 A * | 8/1995 | David et al. | 600/483 |
| 5,447,164 A | 9/1995 | Shaya et al. | 128/710 |
| 5,473,536 A | 12/1995 | Wimmer | 364/400 |
| 5,482,050 A | 1/1996 | Smokoff et al. | 128/710 |
| 5,499,036 A * | 3/1996 | Hauck | 345/3.1 |
| 5,546,580 A * | 8/1996 | Seliger et al. | 707/8 |
| 5,588,109 A | 12/1996 | Dickinson et al. | 395/326 |
| 5,590,650 A | 1/1997 | Genova | 128/630 |
| 5,632,281 A | 5/1997 | Rayburn | 128/719 |
| 5,659,741 A * | 8/1997 | Eberhardt | 707/104.1 |
| 5,678,539 A | 10/1997 | Schubert et al. | 128/204.21 |
| 5,678,568 A | 10/1997 | Uchikubo et al. | 128/897 |
| 5,687,717 A | 11/1997 | Halpern et al. | 128/630 |
| D389,133 S | 1/1998 | Wimmer et al. | D14/114.1 |
| 5,713,350 A | 2/1998 | Yokota et al. | 128/630 |
| 5,715,451 A * | 2/1998 | Marlin | 707/104.1 |
| 5,715,823 A | 2/1998 | Wood et al. | 128/660.01 |
| 5,838,906 A * | 11/1998 | Doyle et al. | 715/501.1 |
| 5,915,379 A | 6/1999 | Wallace et al. | 128/204 |
| 5,921,920 A * | 7/1999 | Marshall et al. | 600/300 |
| 5,931,160 A | 8/1999 | Gilmore et al. | 128/204.21 |
| 5,941,820 A * | 8/1999 | Zimmerman | 600/300 |
| 5,942,986 A | 8/1999 | Shabot et al. | 340/825.44 |
| 5,950,207 A | 9/1999 | Mortimore et al. | 707/104 |
| 6,017,307 A | 1/2000 | Raines | 600/300 |
| 6,017,315 A | 1/2000 | Starr et al. | 600/538 |
| 6,024,089 A | 2/2000 | Wallace et al. | 128/204.21 |
| 6,024,699 A * | 2/2000 | Surwit et al. | 600/300 |
| 6,041,335 A | 3/2000 | Merritt et al. | 707/512 |
| 6,047,259 A * | 4/2000 | Campbell et al. | 705/3 |
| 6,050,940 A | 4/2000 | Braun et al. | 600/300 |
| 6,081,809 A | 6/2000 | Kumagai | 707/104 |
| 6,099,481 A | 8/2000 | Daniels et al. | 600/538 |
| 6,122,351 A | 9/2000 | Schlueter, Jr. et al. | 379/106.02 |
| 6,146,523 A | 11/2000 | Kenley et al. | 210/143 |
| 6,158,432 A | 12/2000 | Biondi et al. | 128/204.21 |
| 6,305,373 B1 * | 10/2001 | Wallace et al. | 128/204.21 |
| 6,390,091 B1 * | 5/2002 | Banner et al. | 128/204.21 |
| 6,584,973 B1 * | 7/2003 | Biondi et al. | 128/204.21 |
| 6,834,647 B2 * | 12/2004 | Blair et al. | 128/204.18 |
| 2005/0125256 A1 * | 6/2005 | Schoenberg et al. | 705/2 |

OTHER PUBLICATIONS http://www.abalk.com/page5.html Anaesthesia, Anaesthesia agent monitor pp. 15.
Narkomed 6000 http://www.nad.com/8bab_narkomed_6000_main_page.htm Dr. Jeffrey Feldman, "Using AV2+ Ventilator Controls In Volume Preset Mode," *Clinical Practice Bulletin*; pp. 4, http://www.nad.com/3CD_Clinical_Bulletin_main.htm.
Solar Unit Manager System General Information.
OS Workstation General Information.
HP M2000A Patient Documentation Center.
Metavision.
Tour Metavision.
Tour Workflow Support.
Tour Data Entry.
Tour Analysis.
Physician Review System General Information.
Solar Lab Access System Functionality Comparison.
Carevue Clinical Information System Agilent Technologies.
HP Carevue Clinical Information System.

\* cited by examiner

Fig. 5

SYSTEM AND METHOD FOR PROCESSING PATIENT INFORMATION

CROSS REFERENCE TO RELATED APPLICATION

This application claims the benefit of a provisional U.S. application, U.S. Ser. No. 60/249,576, filed Nov. 17, 2000, in the names of the present inventors.

FIELD OF THE INVENTION

This invention is generally related to a system and method for processing and displaying of medical information, and more particularly, to processing and displaying of patient data in a network environment.

BACKGROUND OF THE INVENTION

In today's medical environment, various pieces of medical equipment are used to monitor or administer care to patients in, for example, hospital critical care or emergency departments. For example, medical equipment such as ventilators are commonly used to ventilate a patient's lungs with breathing gas, so as to assist a patient when the patient's ability to breathe on his or her own is somehow impaired.

In order to properly administer a piece of medical equipment such as a ventilator, a caregiver must first set up various settings for the ventilator. Examples of commonly required settings to control a ventilator include: Peak Inspiratory Pressure (PIP) setting—limiting the peak pressure during inspiration of air; and Positive End Expiratory Pressure (PEEP) setting—limiting the peak pressure at the end of expiration of air. Many other ventilator settings may also be controlled, depending on the capability of the particular ventilator.

Likewise, medical equipment such as ventilators may also be equipped with various sensors so that a patient caregiver may monitor the condition of the patient through the ventilator. Examples of commonly monitored parameters for a ventilator include Mean Airway Pressure (MAP)—the mean pressure measured within the airway during the breathing cycle; and Tidal Volume Inspired (TVi)—measured volume of gas inhaled by the patient during a normal breath. Of course, different types of medical devices may monitor many other different patient parameters.

In addition, hospitals also have dedicated laboratories to analyze, for example, blood of a patient once the blood has been drawn from the patient. The results of the blood tests may be printed out by a lab technician and given to the health care provider, such as the doctor or nurse in charge of the patient. The care giver can then analyze the results and choose the correct course of treatment for the patient.

SUMMARY OF THE INVENTION

The present inventors recognize that as the number of medical devices used to administer care and monitor patients increases, there is an increasing need for an efficient way to process and display the large amount of data from the various medical devices. Also, medical providers need to input and/or retrieve medical observations, diagnosis and laboratory results freely, remotely and in an efficient manner.

In addition, the present inventors recognize the desirability of a user being able to gather, process and display data remotely from a piece of medical equipment at any location and to use commonly available computing equipment (such as a personal computer, PC), through for example, a local area network and/or a wide area network, such as the internet. Also, it is desirable for a device to be able to process and display pertinent data related to a particular patient at selected time frames, regardless of the source of the data, in an efficient and customizable matter.

Therefore, an internet compatible system for displaying medical information derived from a plurality of sources is described. The system comprises a processor for acquiring data associated with a patient from one of the plurality of sources on the network. The system also prioritizes the acquired data for display in a desired order and/or time frame. A menu generator is used for generating a composite window for displaying the ordered acquired data in a first window together with at least one of user-entered medical notes, medical laboratory results and ventilator data in a second window.

BRIEF DESCRIPTION OF THE DRAWINGS

In the drawing:

FIG. 5 is also another example of a patient summary screen according to the present invention.

DETAILED DESCRIPTION

Figure 1:
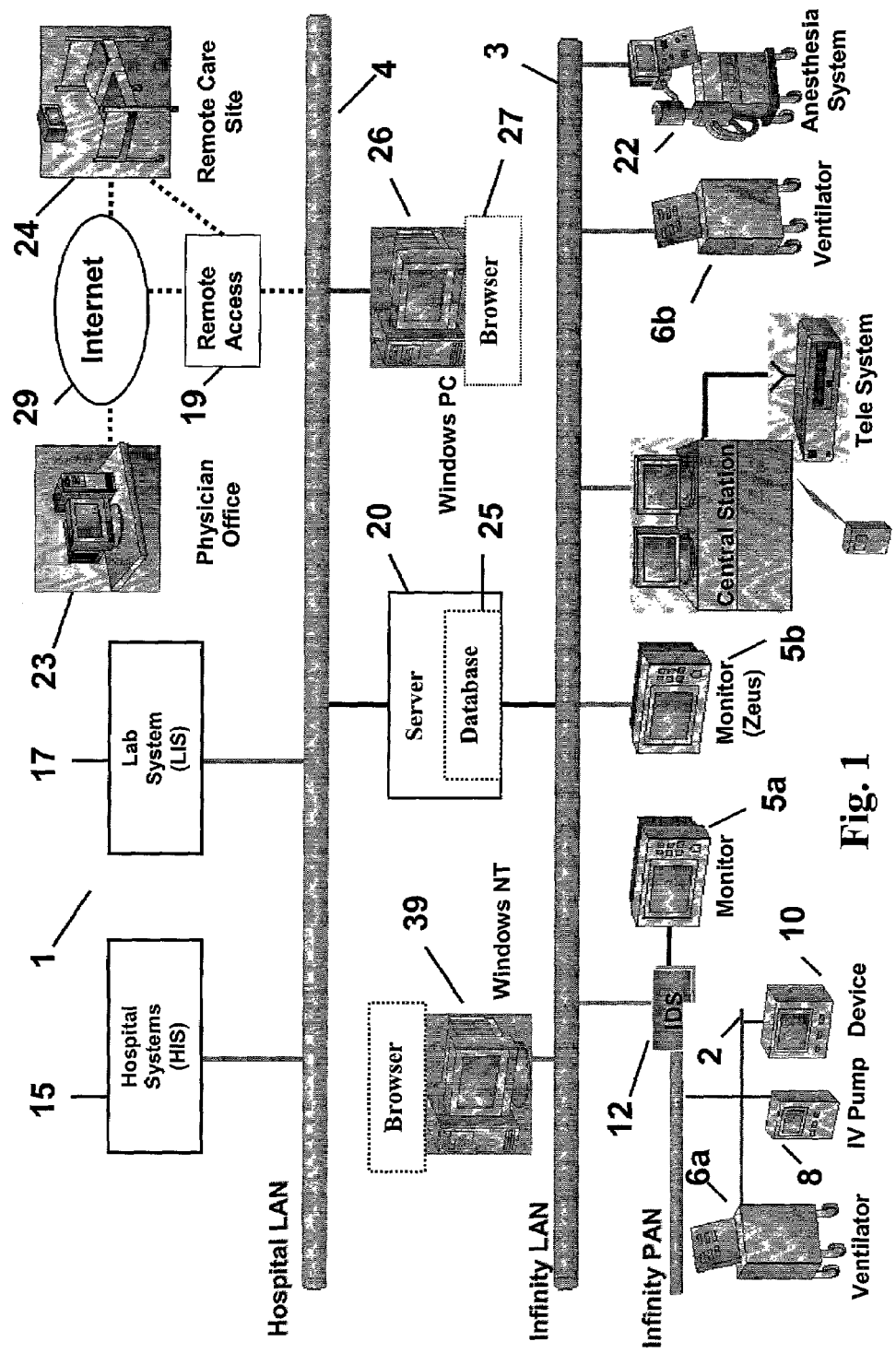
FIG. 1 is a block diagram of a communication network with various devices, according to the principles of the invention.

FIG. 1 is an exemplary block diagram of a communication network according to the principles of the present invention. As shown in FIG. 1, communication network 1 is represented by an IP (Internet Protocol) compatible network with a hierarchy of local area and wide area networks interconnected together. It is to be noted that although the present exemplary hospital or medical network is an IP compatible network, other types of network such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown on FIG. 1, a first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a patient's room to administer care to a particular patient and to monitor the particular patient. Various medical devices may be connected via MIB 2; examples shown in FIG. 1 comprise a ventilator 6a, IV (Intravenous) Pump 8 or other medical device 10. An example of a MIB is an Infinity PAN, marketed by Siemens Medical System.

MIB 2 is typically connected to a second level LAN network 3 through an Interface Docking Station (IDS) device 12, for interfacing to Ethernet-compatible LAN network 3. The higher-level LAN 3 may be for example, an Infinity LAN, marketed by Siemens Medical System. This higher-level LAN 3 is typically, though not necessarily, used by a particular department within a hospital, such as an intensive care department or surgery department, etc., depending on the size of the organizations.

Although not shown in FIG. 1, more than one MIB may be connected to the second level LAN 3, so that more than one patient may be monitored or given care through LAN 3. In addition, medical devices may be connected directly to higher-level LAN 3. For example, as shown in FIG. 1, a ventilator 6b and an anesthesia system 22 are connected directly to LAN 3, without the need to go through a MIB.

Furthermore, LAN 3 may be interconnected to a Hospital LAN backbone 4 which may also be Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 19 which provides remote, secured access from, for example, a remote doctor's office 23 or a remote care site 24, to the various systems and devices on network 1, through for example, the internet 29. Alternatively, a remote site may also access the remote access gateway 19 directly through, for example, a dial-up telephone port, ADSL, or other types of private connection. Remote access gateway 19 may also be part of server 20, to be described below, instead of standing alone as shown in FIG. 1, as well know in the art.

According to the principles of the present invention, a central server 20 resides on LAN 3 for gathering and processing data from ventilators and other medical devices on network 1 for display and control. One skilled in the art can readily recognize that server 20 may reside at any level of the hierarchy of network 1, since all the different levels of local area networks or buses, as well as remote sites in FIG. 1 can be interconnected together. An example of server 20, is a Prometheus server, marketed by Siemens Medical System. The server may be hosted, for example, by a computer system that is capable of running Microsoft NT operating system.

Figure 2:
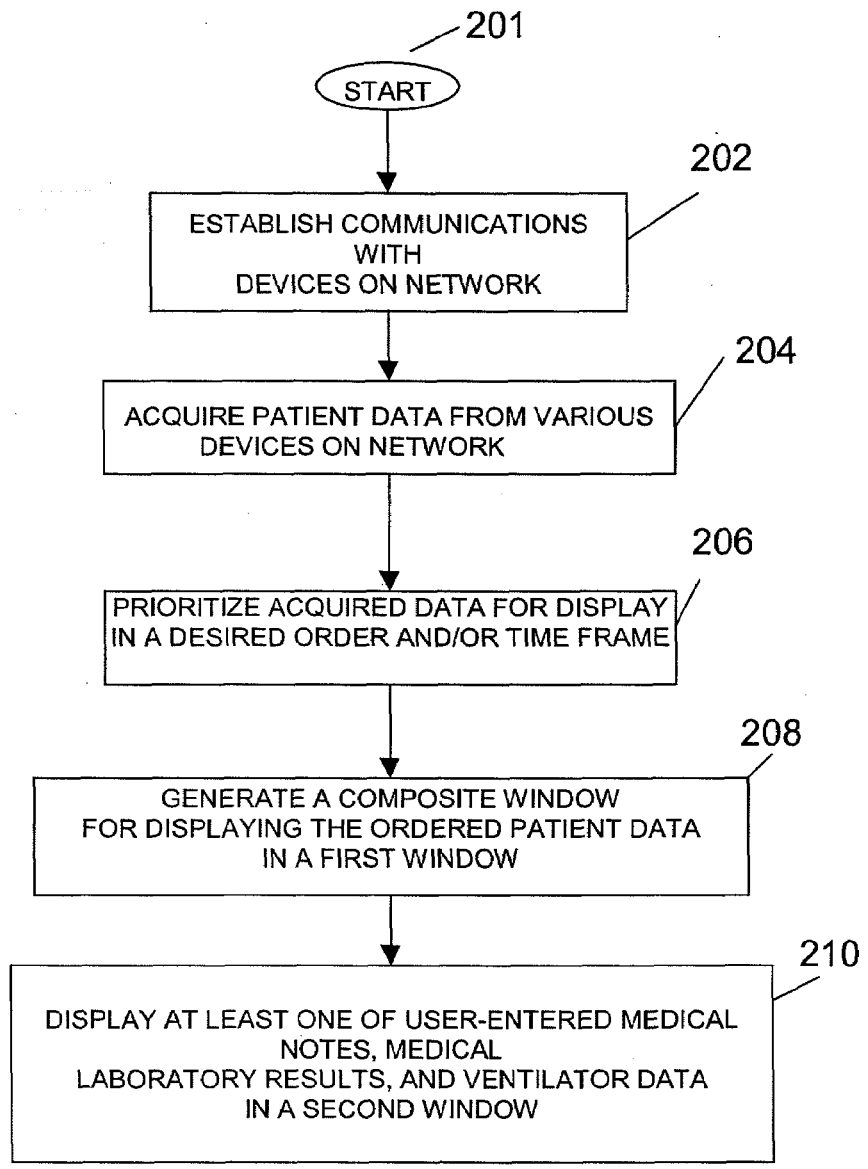
FIGS. 2 represents a flow diagram of a system according to the present invention.

FIG. 2 shows in flow chart form, functions that may be performed in accordance with the present invention. Server 20 first establishes communications with various devices on the network 1 as shown in step 202. This is done, for example, by using IP protocol and the known IP device address for each device on the network 1, in conjunction with a higher application-layer protocol, as well known in the art.

Once communications are established between server 20 and the other devices on network 1, server 20 starts to acquire selected patient data from the various devices on network 1. For example, at step 204, server 20 may acquire ventilator data such as ventilator parameters that are being monitored and ventilator settings selected for each ventilation unit (for example, 6a or 6b on network 1). The server may also acquire patient data from, for example, another medical device (e.g., 10) on network 1.

In addition, server 20 may obtain patient data comprising medical laboratory results that are first entered and stored, for example, in lab system 17 of FIG. 1. Also, server 20 may acquire healthcare provider entered medical notes for display.

At step 206, server 20 in response to a user request then prioritizes these acquired patient data that are stored in server 20, in a desired order and/or time frame for display. The server will then generate a composite window for displaying concurrently, for example, a first window showing ordered patient data and a second window showing at least one of ventilator data, medical laboratory results and user entered medical notes, as shown in steps 208 and 210.

In one aspect of the present invention, a user may use a Microsoft Windows compatible PC 26 or Windows NT compatible PC 29 as shown in FIG. 1, or any other computers capable of running a menu generating program such as a web browser program (e.g., Microsoft Internet Explorer or Netscape Navigator, etc.) to display patient data obtained by server 20. That is, a user may use a web browser on any computer, as long as a communication connection can be made to server 20, to make request and view patient data through server 20. This is advantageous, since a doctor may for example, gain access to a particular ventilator on network 1 from, for example, a remote physician's office 23, without having to access a dedicated terminal. Of course, a user can simply use a keyboard and/or a mouse or any other user interface devices to enter a user selection or request on a user computer, as is known in the art.

Server 20 is therefore capable of formatting patient data acquired from the various devices on network 1 to be compatible with, for example, HTML (HyperText Mark-up Language) programming language for displaying data on a web browser. The server is also responsive to, for example, HTTP (HyperText Transfer Protocol) commands originated from a user's web browser for making a request.

Figure 3:
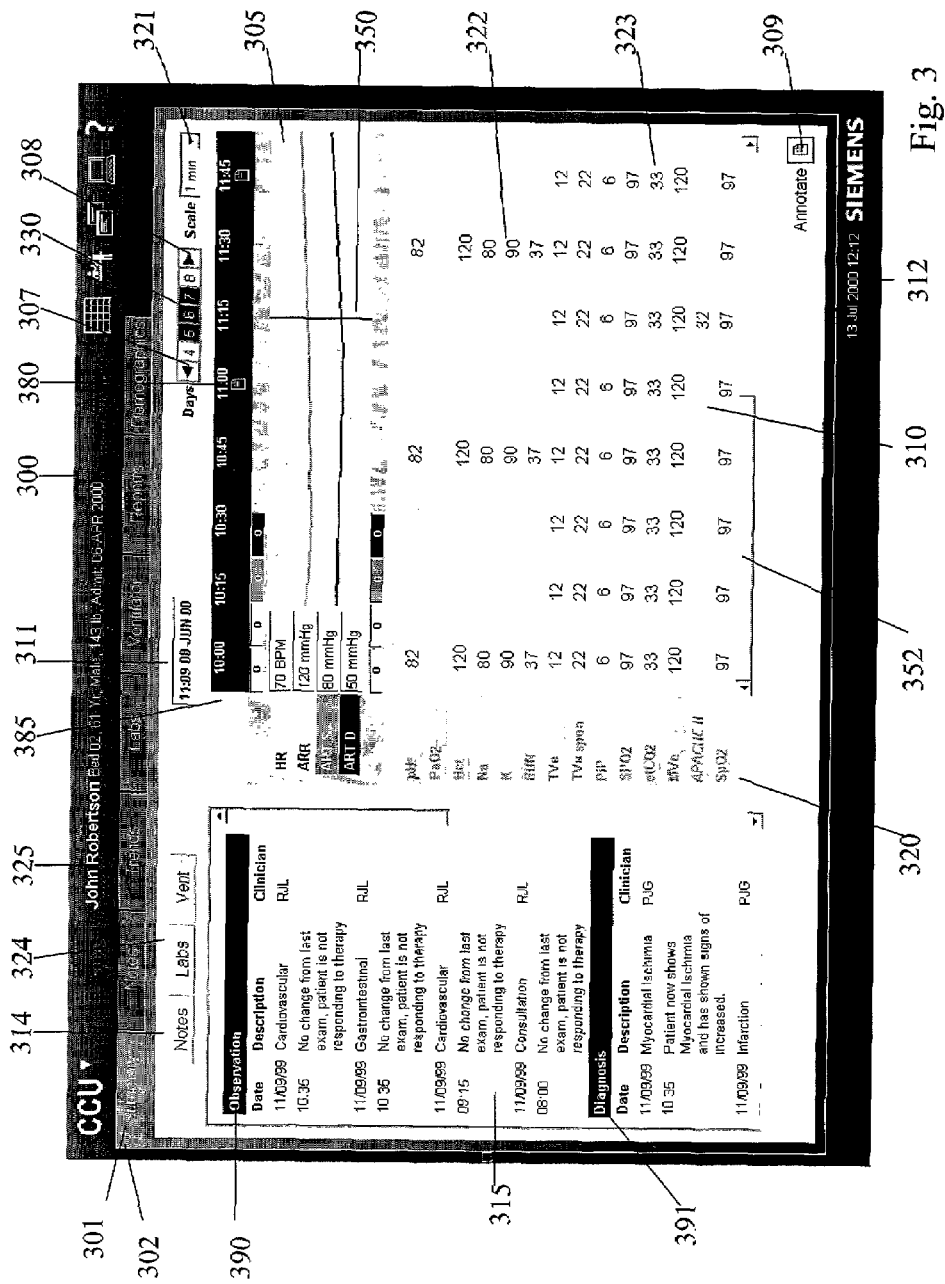
FIG. 3 shows an example of a patient summary screen according to the present invention.

FIG. 3 shows an example of one embodiment of a patient summary screen according to the principles of the present invention. A user may select "Summary" tab 301 on a screen type selection bar 302 to enable the summary screen 300 from a web browser 27 (FIG. 1) of, for example, a user computer 26. Summary screen 300 comprises three data presentation panels 305, 310 and 315; various navigational control icons such as for example, 307, 308, 330; cursor 350 and selection bars 302 and 324; time and date information 311 and 312; and an annotation entry control icon 309.

Graphical trend panel 305 displays a plurality of user specified and prioritized patient trend data which are differentiated. For example, individual trend parameters are differentiated by color. In addition, high and low scale limits for each parameter displayed in panel 305 both appear in respective differentiated colors and in a specific order in which the parameters labels are presented.

Tabular trend panel 310 displays a plurality of user selected patient data in tabular form. For example, the data are presented in respective rows, with parameter or setting labels 320 to the left and actual numerical data 322 extending to the right. The right most column 323 represents the most recently acquired patient data. The resolution of data displayed is determined by "Scale" selection icon 321, which specifies the time scale of the presented data from one column to the next column. This scale selection 321 also determines the precision of the graphical trend data display in panel 305.

In both the graphical trend panel 305 and tabular trend panel 310, patient data may include parameters and/or settings from a ventilator or any other device on network 1, depending on user selection. Also, in both panels, time and trend navigation is provided by date navigator 330, cursor 350, cursor time 311, and a time slider bar 352. A user may specify how many days prior to the current time 312 patient data in both the graphical and tabular panels should be centered on, by using date navigator 330. For example, as shown in FIG. 3, the user has selected for display patient data that have been stored for days 5, 6 and 7 prior to the current date of Jul. 13, 2000. The user may then use time slider bar 352 to focus on the specific time period within the days specified in the date navigator 330, so that the particular time period of interest may be displayed on the screen. As the slider bar 352 is moved, so will the cursor 350 to indicate the selected view time within a time line 385. Also, a cursor time display field 311 will show the precise view time corresponding to the position of the cursor 350.

In another embodiment, a user may simply enter a time and date in the cursor time display field 311 to select the time at which patient data in both panels 305 and 310 will be centered for display. Cursor 350 will then automatically be moved to a time on time line 385 corresponding to the time entered in the cursor time display field 311.

In addition, an annotation function is provided by an annotation icon 309 as shown in FIG. 3. Selection of icon 309 allows a user to annotate a note at the cursor time 311 for any observation that the user may want to enter. Once an annotation is entered, an annotation reminder icon, for example, 380, will be displayed on timeline 385, to let a user knows that an annotated note exists at the corresponding time. To read an annotation, a user may simply select an annotation reminder. The full text of the selected annotation will then be displayed.

Combination data panel 315 permits a user to additionally select for display any one of patient medical notes, patient laboratory results, and ventilator data comprising ventilator parameters and settings, via another user selection bar 324 on top of the combination data panel 315.

For example, FIG. 3 shows an example when "Notes" option 314 has been selected by a user. In this case, combination panel 315 then shows medical notes entered for a particular patient selected, as indicated by for example, patient ID 325. Medical notes may comprise observations 390 and diagnosis 391 entered by health care providers. The medical notes information also include the time and date a particular piece of medical information was entered and by whom, as shown in FIG. 3.

Figure 4:
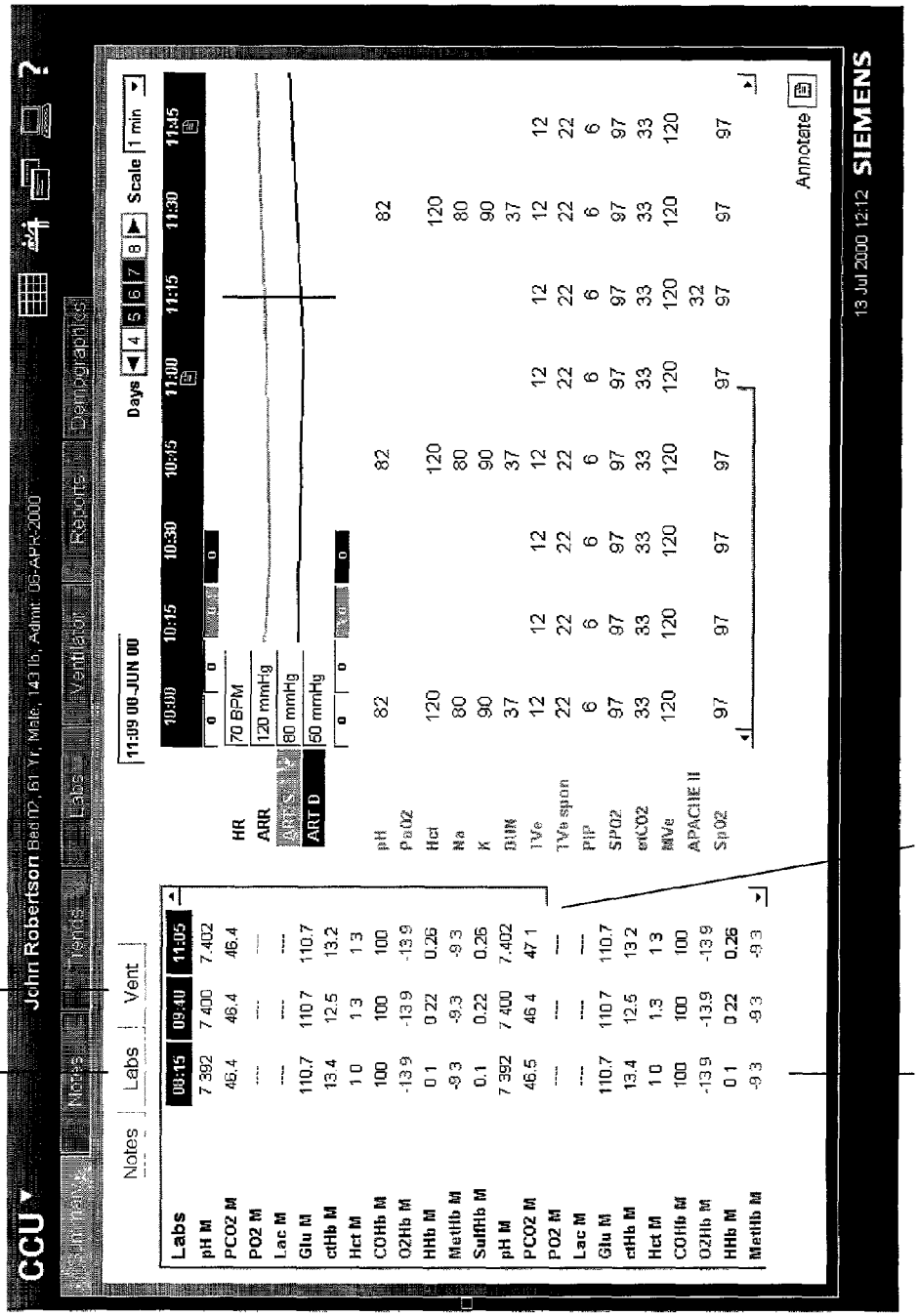
FIG. 4 is another example of a patient summary screen according to the present invention.

In another embodiment, combination panel 315 may display laboratory results for a selected patient in response to a user selecting "Labs" icon 405 on selection bar 324, as shown in FIG. 4. In this case, server 20 (FIG. 1) will communicate with for example, lab system 17 on network 1 to obtain, for example, the most recent laboratory results for the selected patient. FIG. 4 shows, for example, combination panel 315 displaying the three most recent laboratory results in tabular form. A slider bar 410 is provided for a user to view additional laboratory data, by sliding bar 410 up and down.

Figure 5:
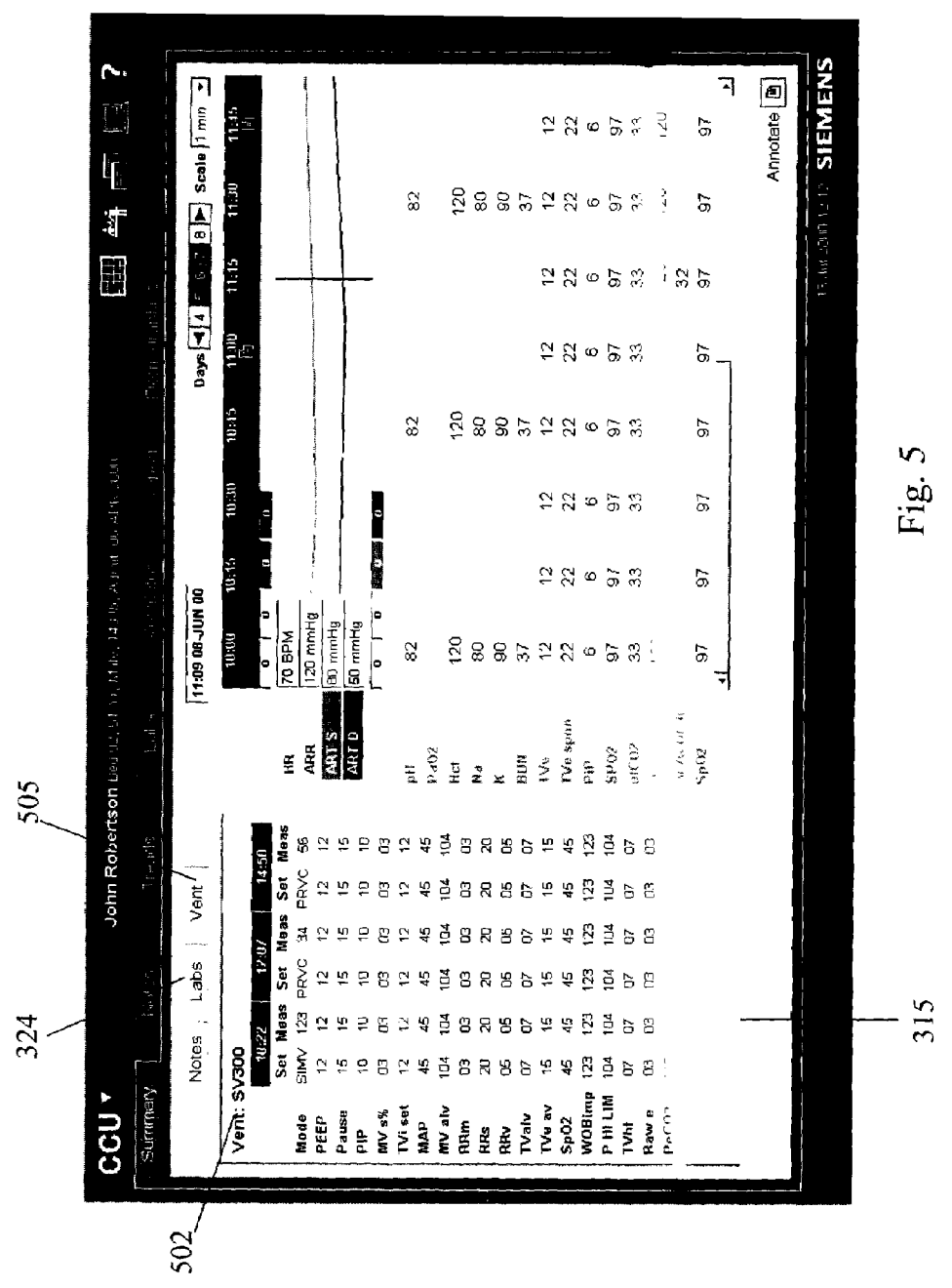

Also, the combination panel 315 may display selected ventilator parameters and/or settings for a selected ventilator, in response to a user selection of "Vent" 505 on selection bar 324, as shown in FIG. 5. The selected ventilator is indicated by a ventilator ID display field 502. As a result, combination panel 315 may display for example, the most three recently acquired ventilator parameters and settings as prioritized by a user, as shown in FIG. 5.

It is to be understood that the embodiments and variations shown and described herein are for illustrations only and that various modifications may be implemented by those skilled in the art without departing from the scope of the invention.

The invention claimed is:

1. In an internet compatible system for displaying medical information derived from a plurality of sources, apparatus comprising:

an acquisition processor for acquiring data associated with a patient from at least one of the plurality of sources, the processor prioritizing the acquired data for display in a desired order;

a display; and a menu generating processor for generating a composite window including a first panel for displaying on said display user specified parameters of said ordered acquired data in a graphical format, a second panel for displaying user specified parameters of said ordered acquired data in tabular format, and a third panel for displaying a user selected one of user-entered medical notes, medical laboratory results, and ventilator data;

wherein said second panel includes a slider bar for navigating through the user specified parameters in tabular format; and said first panel includes a cursor, said cursor being controlled by said slider bar, said slider bar controlling said cursor and enabling concurrent user navigation in both said first and second panels through said user specified parameters in both graphical format and tabular format.

2. The system of claim 1 wherein the ventilator data comprises at least one of a ventilator setting and a ventilator parameter.

3. The system of claim 1 wherein the processor further prioritizing the acquired data for display within a selected time frame.

4. The system of claim 3 wherein a cursor is displayed indicating a selected time during the selected time frame.

5. The system of claim 4 wherein a time display field displays the time corresponding to the selected cursor time.

6. The system of claim 5 further comprising an annotate icon for allowing a user to enter an annotation for the selected time during the selected time period.

7. The system of claim 1 wherein the medical notes further comprising at least one of time of entry, date of entry and person of entry for the medical notes.

8. The system of claim 1 wherein the first window further comprising a graphical data panel and tabular data panel.

9. The system of claim 1 wherein the first window processor prioritizing the acquired data for display in a desired order in response to a user selection.

10. The system of claim 1 wherein said composite window includes a scalability icon for selecting a time scale of the displayed acquired data in both said graphical and tabular format.

11. The system of claim 1 wherein said concurrent navigation comprises navigation through substantially synchronized user specified parameters in graphical format and tabular format.

12. A method for displaying medical information derived from a plurality of sources, comprising the steps of:

acquiring data associated with a patient from at least one of a plurality of sources;

prioritizing the acquired data for display in a desired order; and generating a composite window for displaying said ordered acquired data in a graphical format in a first panel, displaying user specified parameters of said ordered acquired data in tabular format in a second panel, and displaying a user selected one of user-entered medical notes, medical laboratory results, and ventilator data in a third panel navigating through the user specified parameters in tabular format by positioning a slider bar included in said second panel; and controlling a cursor included in said first panel, said cursor being controlled by said slider bar, said slider bar controlling said cursor and enabling concurrent user navigation in both said first and second panels through said user specified parameters in both graphical format and tabular format.

13. The method of claim 12 wherein the ventilator data comprises at least one of ventilator setting and ventilator parameter.

14. The method of claim 12 further comprising the step of displaying the acquired data within a user-selected time frame.

15. The method of claim 14 wherein a cursor is displayed indicating a selected time during the selected time frame.

16. The method of claim 15 further comprising the step of displaying a time corresponding to the selected cursor time.

17. The method of claim 16 further comprising the step of providing an annotate icon for allowing a user to enter an annotation for the selected time during the selected time period.

18. The method of claim 12 further comprising the step of activating a scalability icon included in said composite window for selecting a time scale of the displayed acquired data in both said graphical and tabular format.

19. A method for displaying medical information derived from a plurality of sources on a network, comprising the steps of:
   acquiring data associated with a patient from at least one of the plurality of sources;
   prioritizing the acquired data for display in a desired time period; and
   generating a composite window for displaying said acquired data in a first window together with at least one of user-entered medical notes, medical laboratory results, and ventilator data in a second window
   navigating through the user specified parameters in tabular format by positioning a slider bar included in said second panel; and
   said first panel includes a cursor, said cursor being controlled by said slider bar, said slider bar controlling said cursor and enabling concurrent user navigation in both said first and second panels through said user specified parameters in both graphical and tabular format.

20. The method of claim 19 further comprising the step of displaying the acquired data in different colors.

21. The method of claim 19 further comprising the step of displaying the acquired data in varying scales.

* * * * *